(12) United States Patent
Wachendorff-Neumann et al.

(10) Patent No.: US 8,101,772 B2
(45) Date of Patent: Jan. 24, 2012

(54) FUNGICIDAL ACTIVE SUBSTANCE COMBINATIONS CONTAINING TRIFLOXYSTROBIN

(75) Inventors: Ulrike Wachendorff-Neumann, Neuwied (DE); Astrid Mauler-Machnik, Leichlingen (DE); Christoph Erdelen, Leichlingen (DE); Angelika Lubos-Erdelen, legal representative, Leichlingen (DE); Hirohisa Ohtake, Kanagawa (JP)

(73) Assignee: Bayer Cropscience AG, Monheim (DE)

( * ) Notice: Subject to any disclaimer, the term of this patent is extended or adjusted under 35 U.S.C. 154(b) by 1063 days.

(21) Appl. No.: 10/486,663

(22) PCT Filed: Aug. 5, 2002

(86) PCT No.: PCT/EP02/08702
§ 371 (c)(1),
(2), (4) Date: Jul. 12, 2004

(87) PCT Pub. No.: WO03/015515
PCT Pub. Date: Feb. 27, 2003

(65) Prior Publication Data
US 2005/0009703 A1 Jan. 13, 2005

(30) Foreign Application Priority Data
Aug. 16, 2001 (DE) .................. 101 40 108

(51) Int. Cl.
*C07C 67/02* (2006.01)
*C07D 401/00* (2006.01)

(52) U.S. Cl. ............. 546/274.7; 560/255; 514/341; 514/546

(58) Field of Classification Search .................. None
See application file for complete search history.

(56) References Cited

U.S. PATENT DOCUMENTS

| | | | |
|---|---|---|---|
| 4,742,060 A | 5/1988 | Shiokawa et al. | 514/252 |
| 4,845,106 A | 7/1989 | Shiokawa et al. | 514/342 |
| 4,849,432 A | 7/1989 | Shiokawa et al. | 514/341 |
| 5,001,138 A | 3/1991 | Shiokawa et al. | 514/342 |
| 5,034,404 A | 7/1991 | Uneme et al. | 514/365 |
| 5,175,301 A | 12/1992 | Minamida et al. | 546/272 |
| 5,204,360 A | 4/1993 | Shiokawa et al. | 514/342 |
| 5,214,152 A | 5/1993 | Minamida et al. | 548/181 |
| 5,238,956 A * | 8/1993 | Clough et al. | 514/506 |
| 5,298,507 A | 3/1994 | Shiokawa et al. | 514/256 |
| 5,304,566 A | 4/1994 | Ishimitsu et al. | 514/357 |
| 5,428,032 A | 6/1995 | Shiokawa et al. | 514/226.8 |
| 5,434,181 A | 7/1995 | Kodaka et al. | 514/471 |
| 5,461,167 A | 10/1995 | Shiokawa et al. | 548/167 |
| 5,489,603 A | 2/1996 | Uneme et al. | 514/365 |
| 5,532,365 A | 7/1996 | Kodaka et al. | 544/212 |
| 5,580,889 A | 12/1996 | Shiokawa et al. | 514/343 |
| 5,612,358 A | 3/1997 | Ishimitsu et al. | 514/357 |
| 5,633,375 A | 5/1997 | Uneme et al. | 544/336 |
| 5,750,704 A | 5/1998 | Shiokawa et al. | 546/275.1 |
| 5,789,430 A | 8/1998 | Jautelat et al. | |
| 5,849,768 A | 12/1998 | Minamida et al. | 514/357 |
| 5,852,012 A | 12/1998 | Maienfisch et al. | 514/229.2 |
| 5,859,039 A | 1/1999 | Jautelat et al. | |
| 5,935,981 A | 8/1999 | Minamida et al. | 514/365 |
| 5,998,455 A | 12/1999 | Knauf-Beiter et al. | |
| 6,022,871 A | 2/2000 | Maienfisch et al. | 514/229.2 |
| 6,022,967 A | 2/2000 | Shiokawa et al. | 544/298 |
| 6,124,297 A | 9/2000 | Minamida et al. | 514/255 |
| 6,297,263 B1 | 10/2001 | Dutzmann et al. | |
| 6,297,374 B1 | 10/2001 | Shiokawa et al. | 544/55 |
| 6,306,850 B1 | 10/2001 | Dutzmann et al. | |
| 6,355,634 B1 | 3/2002 | Isenring et al. | |
| 6,376,487 B1 | 4/2002 | Maienfisch et al. | 514/229.2 |
| 6,407,100 B1 | 6/2002 | Isenring et al. | |
| 6,407,248 B1 | 6/2002 | Minamida et al. | 546/331 |
| 6,423,726 B2 | 7/2002 | Dutzmann et al. | |
| 6,559,136 B1 * | 5/2003 | Mauler-Machnik et al. | 514/63 |
| 6,627,753 B1 | 9/2003 | Maienfisch et al. | 544/67 |
| 6,747,047 B2 * | 6/2004 | Lahm et al. | 514/341 |
| 7,008,903 B2 | 3/2006 | Dutzmann et al. | |
| 7,868,025 B2 | 1/2011 | Dutzmann et al. | |
| 2002/0173529 A1 | 11/2002 | Dutzmann et al. | |
| 2003/0232821 A1 | 12/2003 | Maienfisch et al. | 514/229.2 |
| 2005/0101639 A1 | 5/2005 | Ammermann et al. | |
| 2006/0004070 A1 | 1/2006 | Wachendorff-Neumann et al. | |
| 2006/0014738 A1 | 1/2006 | Wachendorff-Neumann et al. | |
| 2006/0035942 A1 | 2/2006 | Wachendorff-Neumann et al. | |
| 2007/0078171 A1 | 4/2007 | Andersch et al. | |
| 2007/0155797 A1 | 7/2007 | Andersch et al. | |
| 2007/0287720 A1 | 12/2007 | Royalty et al. | |
| 2008/0274882 A1 | 11/2008 | Krohn et al. | |

(Continued)

FOREIGN PATENT DOCUMENTS

DE 199 448 590 4/2001

(Continued)

OTHER PUBLICATIONS

Weeds, 15, (month unavailable) 1967, pp. 20-22, S.R. Colby, "Calculating Synergistic and Antagonistic Responses of Herbicide Combinations".
P. Margot et al.: "CGA 279202: A new broad-spectrum strobilurin fungicide", Brighton Crop Protection Conference—Pests and Diseases, Bd. 2, 1998, Seiten 375-382, XP001106474 GB.
Bauer, T.A., et al., "Response of Selected Weed Species to Postemergence Imazethapyr and Bentazon," *Weed Tech.* 9:236-242, The Weed Science Society of America, United States (1995).
Blackshaw, R.E., "HOE-39866 Use in Chemical Fallow Systems," *Weed Tech.* 3:420-428, The Weed Science Society of America, United States (1989).
Blackshaw, R.E., "Synergistic Mixes of DPX-A7881 and Clopyralid in Canola (*Brassica napus*)," *Weed Tech.* 3:690-695, The Weed Science Society of America, United States (1989).
Blackshaw, R.E., et al., "Herbicide Combinations for Postemergent Weed Control in Safflower (*Carthamus tinctorius*)," *Weed Tech.* 4:97-104, The Weed Science Society of America, United States (1990).

(Continued)

*Primary Examiner* — Sharmila G. Landau
*Assistant Examiner* — Barbara Frazier
(74) *Attorney, Agent, or Firm* — Sterne, Kessler, Goldstein & Fox P.L.L.C.

(57) ABSTRACT

The present invention relates to novel active compound combinations comprising a known oxime ether derivative (trifloxystrobin) and imidacloprid, which combinations are highly suitable for controlling phytopathogenic fungi and insects.

5 Claims, No Drawings

U.S. PATENT DOCUMENTS

| | | | |
|---|---|---|---|
| 2009/0306109 | A1 | 12/2009 | Dutzmann et al. |
| 2010/0041659 | A1 | 2/2010 | Dutzmann et al. |
| 2010/0210691 | A1 | 8/2010 | Dutzmann et al. |

FOREIGN PATENT DOCUMENTS

| | | |
|---|---|---|
| DE | 199 53 544 | 5/2001 |
| EP | 0 460 575 | 12/1991 |
| FR | 2 784 011 | 4/2000 |
| WO | 94/29268 | 12/1994 |
| WO | 99/48366 | 9/1999 |
| WO | 00/05959 | 2/2000 |

OTHER PUBLICATIONS

Blouin, D.C., et al., "Analysis of Synergistic and Antagonistic Effects of Herbicides Using Nonlinear Mixed-Model Methodology," *Weed Tech. 18*:464-472, The Weed Science Society of America, United States (2004).

Bradley, P.R., et al., "Response of Sorghum (*Sorghum bicolor*) to Atrazine, Ammonium Sulfate, and Glyphosate," *Weed Tech. 14*:15-18, The Weed Science Society of America, United States (2000).

Buker, III, R.S., et al., "Confirmation and Control of a Paraquat-Tolerant Goosegrass (*Eleusine indica*) Biotype," *Weed Tech. 16*:309-313, The Weed Science Society of America, United States (2002).

Burke, I.C., et al., "CGA-362622 Antagonizes Annual Grass Control with Clethodim," *Weed Tech. 16*:749-754, The Weed Science Society of America, United States (2002).

Flint, J.L., et al., "Analyzing Herbicide Interactions, A Statistical Treatment of Colby's Method," *Weed Tech. 2*:304-309, The Weed Science Society of America, United States (1988).

Gillespie, G.R., and Nalewaja, J.D., "Wheat (*Triticum aestivum*) Response to Triallate Plus Chlorsulfuron," *Weed Tech. 3*:20-23, The Weed Science Society of America, United States (1989).

Green, J.M., et al., "Metribuzin and Chlorimuron Mixtures for Preemergence Broadleaf Weed Control in Soybeans, *Glycine max*," *Weed Tech. 2*:355-363, The Weed Science Society of America, United States (1988).

Harker, N.K., and O'Sullivan, P.A., "Synergistic Mixtures of Sethoxydim and Fluazifop on Annual Grass Weeds," *Weed Tech. 5*:310-316, The Weed Science Society of America, United States (1991).

Kent, L.M., et al., "Effect of Ammonium Sulfate, Imazapyr, and Environment on the Phytotoxicity of Imazethapyr," *Weed Tech. 5*:202-205, The Weed Science Society of America, United States (1991).

Kotoula-Syka, E., et al., "Interactions between SAN 582H and Selected Safeners on Grain Sorghum (*Sorghum bicolor*) and Corn (*Zea mays*)," *Weed Tech. 10*:299-304, The Weed Science Society of America, United States (1996).

Lanclos, D.Y., et al., "Glufosinate Tank-Mix Combinations in Glufosinate-Resistant Rice (*Oryza sativa*)," *Weed Tech. 16*:659-663, The Weed Science Society of America, United States (2002).

Norris, J.L., et al., "Weed Control from Herbicide Combinations with Three Formulations of Glyphosate," *Weed Tech. 15*:552-558, The Weed Science Society of America, United States (2001).

Novosel, K.M., et al., "Metolachlor Efficacy as Influenced by Three Acetolactate Synthase-Inhibiting Herbicides," *Weed Tech. 12*:248-253, The Weed Science Society of America, United States (1998).

Palmer, E.W., et al., "Broadleaf Weed Control in Soybean (*Glycine max*) with CGA-277476 and Four Postemergence Herbicides," *Weed Tech. 14*:617-623, The Weed Science Society of America, United States (2000).

Salzman, F.P., and Renner, K.A., "Response of Soybean Combinations of Clomazone, Metribuzin, Linuron, Alachlor, and Atrazine," *Weed Tech. 6*:922-929, The Weed Science Society of America, United States (1992).

Scott, R.C., et al., "Spray Adjuvant, Formulation, and Environmental Effects of Synergism from Post-Applied Tank Mixtures of SAN 582H with Fluazifop-P, Imazethapyr, and Sethoxydim," *Weed Tech. 12*:463-469, The Weed Science Society of America, United States (1998).

Shaw, D.R. and Arnold, J.C., "Weed Control from Herbicide Combinations with Glyphosate," *Weed Tech. 16*:1-6, The Weed Science Society of America, United States (2002).

Snipes, C.E., and Allen, R.L., "Interaction of Graminicides Applied in Combination with Pyrithiobac," *Weed Tech. 10*:889-892, The Weed Science Society of America, United States (1996).

Wehtje, G. and Walker, R.H., "Interaction of Glyphosate and 2,4-DB for the Control of Selected Morningglory (*Ipomoea* spp.) Species," *Weed Tech. 11*:152-156, The Weed Science Society of America, United States (1997).

Zhang, W., et al., "Fenoxaprop Interactions for Barnyardgrass (*Echinochloa crus-galli*) Control in Rice," *Weed Tech. 19*:293-297, The Weed Science Society of America, United States (2005).

Rummens, F.H.A., "An Improved Definition of Synergistic and Antagonistic Effects," Weed Science 23(1):4-6, The Weed Science Society of America, United States (1975).

Tomlin, C., ed., *The Pesticide Manual*, Eleventh Edition, 1242-1245, British Crop Protection Council, Farnham, UK (1997).

Opposition Proceeding in European Patent No. EP-B-1482798, Mar. 5, 2007-Nov. 9, 2009.

Prosecution History of European Patent Appl. No. 03735610.2 (European Counterpart of U.S. Appl. No. 10/518,742), Jul. 13, 2006-Sep. 25, 2009.

Partial English language translation of Prosecution History of European Patent Appl. No. 03735610.2, Jul. 13, 2006-Sep. 25, 2009.

Partial English language translation of Opposition Proceeding in European Patent No. EP-B-1482798, Feb. 26, 2007-Nov. 9, 2009.

"Azoxystrobin data sheet," Compendium of Pesticide Common Names, accessed at http://www.alanwood.net/pesticides/azoxystrobin.html, accessed on Apr. 8, 2009, 1 page.

"Kresoxim-methyl data sheet," Compendium of Pesticide Common Names, accessed at http://www.alanwood.net/pesticides/kresoxim-methyl.html, accessed on Apr. 8, 2009, 1 page.

"Metominostrobin data sheet," Compendium of Pesticide Common Names, accessed at http://www.alanwood.net/pesticides/metominostrobin.html, accessed on Apr. 8, 2009, 1 page.

Declaration of Heike Hungenberg Under 37 C.F.R. § 1.132, dated Jul. 25, 2011, submitted Jul. 27, 2011, in U.S. Appl. No. 11/722,648.

\* cited by examiner

FUNGICIDAL ACTIVE SUBSTANCE COMBINATIONS CONTAINING TRIFLOXYSTROBIN

The present patent application has been filed under 35 U.S.C. 371 as a national stage application of PCT/EP02/08702, filed Aug. 5, 2002, which was published in German as International Patent Publication WO 03/015515 on Feb. 27, 2003, which is entitled to the right of priority of German Patent Application 101 40 108.6, filed Aug. 16, 2001.

The present invention relates to novel active compound combinations comprising a known oxime ether derivative and known insecticidally active compounds, which combinations are highly suitable for controlling phytopathogenic fungi and insects.

It is already known that methyl 2-[α-{[(α-methyl-3-trifluoromethyl-benzyl)imino]oxy}-o-tolyl]-glyoxylate O-methyl oxime has fungicidal properties (cf. EP-A1-460 575). The activity of this substance is good; however, at low application rates it is sometimes unsatisfactory.

Furthermore, it is known that imidacloprid (cf. EP-A-192 060 or Pesticide Manual, 9th Edition (1991), page 491), thiacloprid (cf. EP-A-235 725), acetamiprid (WO 91/04965), nitenpyram (cf. EP-A-302 389), thiamethoxam (cf. EP A 580 553), clothianidin (cf. EP-A-376 279) and dinotefuran (cf. EP-A -649845) have insecticidal properties. The activity of these substances is good; however, at low application rates it is sometimes unsatisfactory.

It has now been found that the novel active compound combinations of methyl 2-[α-{[(α-methyl-3-trifluoromethylbenzyl)imino]oxy}-o-tolyl]-glyoxylate O-methyl oxime of the formula (I)

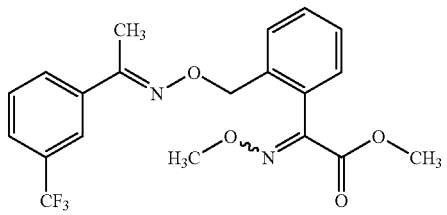

(trifloxystrobin)

and (1) 1-[(6-chloro-3-pyridinyl)methyl]-N-nitro-2-imidazolidineimine (reference: EP-A-192 060) of the formula (II)

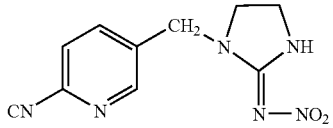

(imidacloprid)

and/or (2) the thiazolidine (reference: EP-A-235 725) of the formula (III)

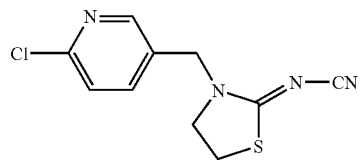

(thiacloprid)

and/or (3) the chloronicotinyl compound (reference: WO 91/04965) of the formula (IV)

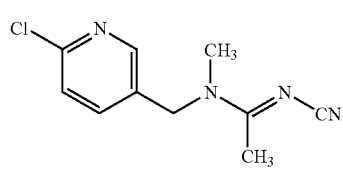

(acetamiprid)

and/or (4) the chloronicotinyl compound (reference: EP-A-302 389) of the formula (V)

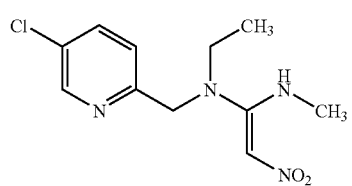

(nitenpyram)

and/or (5) the neonicotinoid (reference: EP-A-580 553) of the formula (VI)

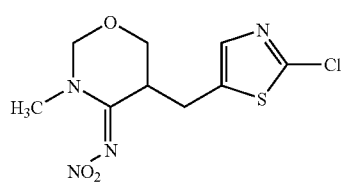

(thiamethoxam)

and/or (6) the neonicotinoid (reference: EP-A-376 279) of the formula (VII)

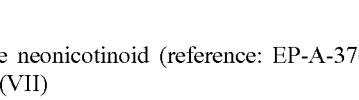

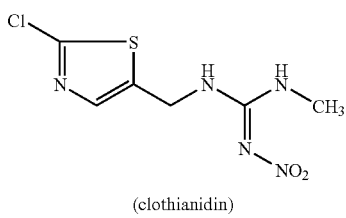

(clothianidin)

and/or (7) the neonicotinoid (reference: EP-A-649 845) of the formula (VIII)

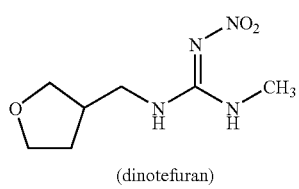

(dinotefuran)

have very good fungicidal and insecticidal properties.

Surprisingly, the fungicidal and insecticidal action of the active compound combinations according to the invention is considerably higher than the sum of the actions of the individual active compounds. What is present is therefore an unforeseeable true synergistic effect and not just a combination of actions.

As can be seen from the structural formula of the active compound of the formula (I), the compound can be present as E or Z isomer. The product can therefore be present as a mixture of different isomers or else in the form of a single isomer. Preference is given to compounds of the formula (I) in which the compound of the formula (I) is present as E isomer.

The active compound of the formula (I) is known (compare, for example, EP-A1-460 575). The active compounds of the formulae (II), (III), (IV), (V), (VI), (VII) and (VIII) are likewise known (cf the given references).

In addition to at least one active compound of the formula (I), the active compound combinations according to the invention comprise the active compound imidacloprid. Additionally, they may also comprise further fungicidally or insecticidally active components.

The synergistic effect is particularly pronounced when the active compounds in the active compound combinations according to the invention are present in certain weight ratios. However, the weight ratios of the active compounds in the active compound combinations can be varied within a relatively wide range.

In general, from 0.1 to 10 parts by weight, preferably from 0.2 to 2 parts by weight, of active compound of the formula (II), from 0.05 to 20 parts by weight, preferably from 0.1 to 10 parts by weight, of active compound of the formula (III), from 0.05 to 20 parts by weight, preferably from 0.1 to 10 parts by weight, of active compound of the formula (IV), from 0.05 to 20 parts by weight, preferably from 0.1 to 10 parts by weight, of active compound of the formula (V), from 0.05 to 20 parts by weight, preferably from 0.1 to 10 parts by weight, of active compound of the formula (VI), from 0.05 to 20 parts by weight, preferably from 0.1 to 10 parts by weight, of active compound of the formula (VII), from 0.05 to 20 parts by weight, preferably from 0.1 to 10 parts by weight, of active compound of the formula (VIII), are present per part by weight of active compound of the formula (I).

The active compound combinations according to the invention have potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, *Ascomycetes*, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or

*Pseudoperonospora cubensis;*

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea*

(conidia form: *Drechslera*, syn: *Helminthosporium*);

Cochliobolus species, such as, for example, *Cochliobolus sativus*

(conidia form: *Drechslera*, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii;*

*Pyricularia* species, such as, for example, *Pyricularia oryzae;*

*Fusarium* species, such as, for example, *Fusarium culmorum;*

*Botrytis* species, such as, for example, *Botrytis cinerea;*

*Septoria* species, such as, for example, *Septoria nodorum;*

*Leptosphaeria* species, such as, for example, *Leptosphaeria nodorum;*

*Cercospora* species, such as, for example, *Cercospora canescens;*

*Altemaria* species, such as, for example, *Altemaria* brassicae; and

*Pseudocercosporella* species, such as, for example, *Pseudocercosporella herpotrichoides*.

The active compound combinations according to the invention also have very good fortifying action in plants. Accordingly, they can be used for mobilizing the defences of the plant against attack by undesirable microorganisms.

In the present context, plant-fortifying (resistance-inducing) active compound combinations and/or substances are to be understood as meaning those substances which are capable of stimulating the defence system of plants such that, when the treated plants are subsequently inoculated with undesirable microorganisms, they show substantial resistance against these microorganisms.

In the present case, undesirable microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treat-ment of the plants with the active compound combinations.

The fact that the active compound combinations are well tolerated by plants at the concentrations required for controlling plant diseases permits the treatment of above-ground parts of plants, of propagation stock and seeds, and of the soil.

The active compounds according to the invention can be used with particularly good results for controlling diseases in rice, such as, for example, *Pyricularia* and *Rhizoctonia*, foliar and ear diseases in cereals, in particular *Leptosphaeria, Septoria, Pyrenophora* spp., *Erysiphe, Puccinia, Fusarium* spp., *Microdochium nivale, Rhizoctonia* spp; diseases of vegetables and potatoes, such as, for example, *Cercospora, Rhizoctonia, Altemaria, Cladosporium, Colletotrichum, Diaporthe, Puccinia, Mycosphaerella, Phoma, Leveillula, Phytophthora, Pseudoperonospora, Botrytis*, and against fungal attack in fruits including citrus fruits, such as, for example, *Elsinoe,* Gloedes, *Venturia, Alternaria, Coccomyces, Diaporthe, Gymnosporangium, Mycosphaerella, Phoma, Monilinia*, and also fungal diseases in grapevines, tea, tobacco, hops, coffee, bananas, nuts and ornamental plants, for example *Uncinula* and *Plasmopara* on grapevines, *Cercospora,* Cofletotrichum, *Mycosphaerella, Phoma, Alternaria*.

The active compound combinations according to the invention are also suitable for increasing the yield of crops. In addition, they show reduced toxicity and are well tolerated by plants.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment according to the invention of the plants and parts of plants with the active compound combinations is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

In the protection of materials, the active compound combinations according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fingi (*Basidiomycetes*), and against slime organisms and algae.

Microorganisms of the following genera may be mentioned as examples:

*Altemaria*, such as *Altemaria* tenuis,
*Aspergillus*, such as *Aspergillus niger,*
Chaetomium, such as Chaetomium globosum,
*Coniophora, such as Coniophora puetana,*
*Lentinus*, such as *Lentinus* tigrinus,
*Penicillium*, such as *Penicillium* glaucum,
*Polyporus*, such as *Polyporus* versicolor,
*Aureobasidium*, such as *Aureobasidium pullulans,*
Sclerophoma, such as Sclerophoma pityophila,
*Trichoderma*, such as *Trichoderma viride,*
*Escherichia*, such as *Escherichia coli,*
*Pseudomonas*, such as *Pseudomonas aeruginosa*, and
*Staphylococcus*, such as *Staphylococcus aureus.*

Depending on their particular physical and/or chemical properties, the active compound combinations can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:

Fungicides:

aldimorph, ampropylfos, ampropylfos-potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capropamid, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazolei, etaconazole, ethirimol, etridiazole, famoxadon, fenapanil, fenarimol, fenbuconazole, fenfuram, fenhexamid, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetylsodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, iprovalicarb, iirumanycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxirn, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), quinoxyfen, sulphur and sulphur preparations, spiroxamine, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziram and also Dagger G,

OK-8705,

OK-8801,

α-(1,1-diinethylethyl)-α-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-α-methoxy-α-methyl-1H-1,2,4-triazole-1-ethanol,

α-(5-methyl-1,3-dioxan-5-yl)-β-[[4-(trifluoromethyl) -phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-(2,4-dichlorophenyl)-2-(1H-1,2,4-triazol-1-yl)-ethanone O-(phenyhnethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoro-methyl-1,3-thiazole-5-carboxanilide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl)-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine-hydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methaneimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
4-[(3,4-dimethoxyphenyl)-3-(4-fluorophenyl)-acryloyl]-morpholine.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:
abamectin, acephate, acequinocyl, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis,* baculoviruses, *Beauveria bassiana, Beauveria tenella,* bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboximn, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, dicofol, diflubenzuron, dimethoate, dimethylvinphos, dinotefuran, diofenolan, disulfoton, docusat-sodium, dofenapyn,
eflusilanate, emamectin, empenthrin, endosulfan, *Entomopfthora* spp., esfenvalerate, ethiofencarb, ethion, ethiprole, ethoprophos, etofenprox, etoxazole, etrimfos,
fenamiphos, fenazaquin, fenbutatin oxide, fenitrothion, fenothiocarb, fenoxacrinm, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses,
lambda-cyhalothrin, lufenuron,
malathion, mecarbam, metaldehyde, methamidophos, *Metharhizium anisopliae, Metharhizium flavoviride,* methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
Paecilomyces fumosoroseus, parathion A, parathion M, permethrin, phenthoate, phorat, phosalone, phosmet, phosphamidon, phoxim, pirimicarb, pirimiphos A, pirimiphos M, profenofos, promecarb, propargite, propoxur, prothiofos, prothoat, pymetrozine, pyraclofos, pyresmethrin, pyrethrum, pyridaben, pyridathion, pynmidifen, pyriproxyfen, quinalphos, ribavirin, salithion, sebufos, silafluofen, spinosad, spirodiclofen, spiromesifen, sulfotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii,*

YI 5302 zeta-cypermethrin, zolaprofos (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-ditnethyl-N-nitro-1,3,5-triazine- 2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-aniino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3 (2H)-pyridazinone, 4-chloro-5-[(6-chloro-3-pyridinyl)methoxy]-2-(3,4-dichlorophenyl)-3 (2H)-pyridazinone,

*Bacillus thuringiensis* strain EGii-2348,

[2-benzoyl-1-(1,1-dimethylethyl)-hydrazinobenzoic acid, 2,2-dimethyl-3-(2,4-dichlorophenyl)-2-oxo-1-oxaspiro[4.5] dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3 (4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N''-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate, N-cyanomethyl-4-trifluoromethyl-nicotinamide, 3,5-dichloro-1-(3,3-dichloro-2-propenyloxy)-4-[3-(5-trifluoromethylpyridine-2-yloxy)-propoxy]-benzene.

A mixture with other known active compounds, such as herbicides, or with fertilizers and growth regulators, is also possible.

In addition, the active compound combinations according to the invention also have very good antimycotic activity. They have a very broad antimycotic activity spectrum in particular against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and audouinii. The list of these fungi by no means limits the mycotic spectrum covered, but is only for illustration.

The active compound combinations can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compound combinations by the ultra-low-volume method, or to inject the active compound preparation or the active compound combination itself into the soil. It is also possible to treat the seeds of the plants.

When using the active compound combinations according to the invention as fungicides, the application rates can be varied within a relatively wide range, depending on the kind of application. For the treatment of parts of plants, the active compound combination application rates are generally between 0.1 and 10,000 g/ha, preferably between 10 and 1000 g/ha. For seed dressing, the active compound combination application rates are generally between 0.001 and 50 g per kilogram of seed, preferably between 0.01 and 10 g per kilogram of seed. For the treatment of the soil, the active compound combination application rates are generally between 0.1 and 10,000 g/ha, preferably between 1 and 5000 g/ha.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having certain properties ("traits") which have been obtained by conventional breeding, by mutagenesis or by recombinant DNA techniques. This can be varieties, bio- and genotypes Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compound combination which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferred and to be treated according to the invention include all plants which, in the genetic modification, received genetic material which imparts particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, nematodes, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are particularly emphasized are the increased defence of the plants against insects by toxins formed in the plants, in particular those formed by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants to fingi, bacteria and viruses by systemic acquired resistance (SAR), systemin, phytoalexins, elicitors, and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes in question which impart the desired traits can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Links (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still-to-be-developed genetic traits, which plants will be developed and/or marketed in the future.

The plants listed can be treated in a particularly advantageous manner with the active compound mixtures according to the invention. The preferred ranges stated above for the active compound combination also apply to the treatment of these plants.

The active compound combinations are suitable for controlling animal pests, in particular insects, arachnids and nematodes, found in agriculture, in forests, in the protection of stored products and materials and in the hygiene sector, and they are tolerated well by plants and have favourable homeotherm toxicity. They can preferably be used as crop protection compositions. They are active against normally sensitive and resistant species, and against all or individual developmental stages.

The abovementioned pests include:

From the order of the Isopoda, for example, Oniscus asellus, Armadillidium vulgare, Porcellio scaber.

From the order of the Diplopoda, for example, Blaniulus guttulatus.

From the order of the Chilopoda, for example, Geophilus carpophagus, *Scutigera* spp.

From the order of the Symphyla, for example, Scutigerella immaculata.

From the order of the Thysanura, for example, Lepisma saccharina.

From the order of the Collembola, for example, Onychiurus armatus.

From the order of the Orthoptera, for example, Acheta domesticus, *Gryllotalpa* spp., Locusta migratoria migratorioides, *Melanoplus* spp., Schistocerca gregaria.

From the order of the Blattaria, for example, *Blatta orientalis, Periplaneta americana*, Leucophaea maderae, *Blattella germanica*.

From the order of the *Dermaptera*, for example, Forficula auricularia.

From the order of the *Isoptera*, for example, *Reticulitermes* spp.

From the order of the Phthiraptera, for example, Pediculus humanus corporis, *Haematopinus* spp., *Linognathus* spp., *Trichodectes* spp., *Damalinia* spp.

From the order of the *Thysanoptera*, for example, Hercinothrips femoralis, *Thrips tabaci, Thrips* palni, *Frankliniella occidentalis*.

From the order of the Heteroptera, for example, *Eurygaster* spp., *Dysdercus* intermedius, Piesma quadrata, Cirnex lectularius, Rhodnius prolixus, *Triatoma* spp.

From the order of the *Homoptera*, for example, Aleurodes brassicae, Bernisia tabaci, *Trialeurodes* vaporariorum, *Aphis gossypii, Brevicoryne brassicae*, Cryptomyzus ribis, *Aphis fabae*, Aphis pomi, Eriosoma lanigerum, *Hyalopterus* arundinis, Phylloxera vastatrix, *Pemphigus* spp., *Macrosiphum avenae, Myzus* spp., Phorodon humuli, *Rhopalosiphum padi, Empoasca* spp., Euscelis bilobatus, *Nephotettix cincticeps*, Lecanium corni, Saissetia oleae, Laodelphax striatellus, *Nilaparvata lugens, Aonidiella* aurantii, Aspidiotus hederae, *Pseudococcus* spp., *Psylla* spp.

From the order of the *Lepidoptera*, for example, *Pectinophora gossypiella*, Bupalus piniarius, Cheimatobia brumata, Lithocolletis blancardella, *Hyponomeuta padella, Plutella xylostella*, Malacosoma neustria, *Euproctis chrysorrhoea, Lymantria* spp., *Bucculatrix thurberiella*, Phyllocnistis citrella, *Agrotis* spp., *Euxoa* spp., *Feltia* spp., Earias insulana, *Heliothis* spp., *Mamestra brassicae*, Panolis flammea, *Spodoptera* spp., *Trichoplusia ni*, Carpocapsa pomonella, *Pieris* spp., *Chilo* spp., Pyrausta nubilalis, *Ephestia* kuehniella, *Galleria mellonella, Tineola* bisselliella, Tinea pellionella, Hofinannophila pseudopretella, Cacoecia podana, Capua reticulana, Choristoneura fumiferana, Clysia ambiguella, Homona magnanima, Tortrix viridana, *Cnaphalocerus* spp.

From the order of the *Coleoptera*, for example, Anobium punctatum, Rhizopertha dominica, Bruchidius obtectus, *Acanthoscelides obtectus*, Hylotrupes bajulus, Agelasfica alni, *Leptinotarsa decemlineata*, Phaedon cochleariae, *Diabrotica* spp., Psylliodes chrysocephala, *Epilachna varivestis*, *Atomaria* spp., Oryzaephilus surinamensis, *Anthonomus* spp., *Sitophilus* spp., Otiorrhynchus sulcatus, Cosmopolites sordidus, Ceuthorrhynchus assimilis, *Hypera postica*, *Dermestes* spp., *Trogoderma* spp., *Anthrenus* spp., *Attagenus* spp., *Lyctus* spp., *Meligethes aeneus*, *Ptinus* spp., Niptus hololeucus, Gibbium psylloides, *Tribolium* spp., *Tenebrio molitor*, *Agriotes* spp., *Conoderus* spp., Melolontha melolontha, Amphimallon solstitialis, Costelytra zealandica, *Lissorhoptrus oryzophilus*, *Oulema oryzae*.

From the order of the *Hymenoptera*, for example, *Diprion* spp., *Hoplocampa* spp., *Lasius* spp., *Monomorium pharaonis*, *Vespa* spp. From the order of the *Diptera*, for example, *Aedes* spp., *Anopheles* spp., *Culex* spp., *Drosophila melanogaster*, *Musca* spp., *Fannia* spp., *Calliphora erythrocephala*, *Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., Bibio hortulanus, Oscinella frit, *Phorbia* spp., Pegomyia hyoscyami, Ceratitis capitata, Dacus oleae, Tipula paludosa, *Hylemyia* spp., *Liriomyza* spp.

From the order of the *Siphonaptera*, for example, *Xenopsylla* cheopis, *Ceratophyllus* spp.

From the class of the Arachnida, for example, Scorpio maurus, Latrodectus mactans, Acarus siro, *Argas* spp., *Ornithodoros* spp., Dermanyssus gallinae, *Eriophyes* ribis, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., Bryobia praetiosa, *Panonychus* spp., *Tetranychus* spp., *Hemitarsonemus* spp., *Brevipalpus* spp.

The plant-parasitic nematodes include, for example, *Pratylenchus* spp., Radopholus similis, Ditylenchus dipsaci, *Tylenchulus* semipenetrans, *Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

The active compounds according to the invention can be used with particularly good results for controlling pests of the order:

Homoptera: *Trialeurodes* vaporariorum, *Bemisia tabaci*, scale-bugs and mealy-bugs, such as, for example, Pseudococcus comstocki, *Aonidiella* aurantii, Unaspis yanonensis, Ceroplastes ceriferus, and also aphids and leafhoppers shield bugs of the order Heteroptera Thysanoptera: *Franklinella occidentalis*, Scirtothrips dorsalis, *Thrips* palmi, *Thrips* tabaci Lepidoptera: leaf-mining caterpillars, such as, for example, Lyonetia clerkella, Phyllocnistis citrella and also *Pieris brassicae*, Hellula undalis, Carposina niponensis, *Plutella xylostella*, Gracillaria theivora, *Papilio* spp.

Coleoptera: Oxycetonia jucunda, *Lissorhoptrus oryzophilus*, *Sphenophorus* venatus vestitus, *Carpophilus* spp., and also wire-worms, flea beetles, chafers, longhorn beetles, weevils and leaf-eating beetles.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms. When used against hygiene pests and stored-product pests, the active compound combinations are distinguished by an excellent residual action on wood and clay as well as good stability to alkali on limed substrates.

The active compound combinations according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, head lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.

From the order *Diptera* and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis*, *Periplaneta americana*, *Blattella germanica*, *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp., *Varroa* spp.

From the order of the Actinedida (Prostigmata) and Acaridida (Astigmata), for example, *Acarapis* spp., *Cheyletiella* spp., *Omithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compound combinations according to the invention.

The active compound combination according to the invention is used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally and the like), implants, by nasal administration, by dermal administration in the form of, for example, immersing or dipping, spraying, pouring-on, spotting-on, washing, dusting, and with the aid of active-compound-comprising moulded articles such as collars, ear tags, tail tags, limb bands, halters, marking devices and the like.

When used for cattle, poultry, domestic animals and the like, the active compound combination can be applied as formulations (for example powders, emulsions, flowables) comprising the active compounds in an amount of 1 to 80% by weight, either directly or after 100- to 10 000-fold dilution, or they may be used as a chemical dip.

Moreover, it has been found that the active compound combinations according to the invention show a potent insecticidal action against insects which destroy industrial materials.

The following insects may be mentioned by way of example and with preference, but not by way of limitation:
Beetles such as Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec., Tryptodendron spec., Apate monachus, Bostrychus capucins, Heterobostrychus brunneus, Sinoxylon spec., Dinoderus minutus.
Dermapterans such as Sirex juvencus, Urocerus gigas, Urocerus gigas taignus, Urocerus augur.
Termites such as Kalotermes flavicollis, Cryptotermes brevis, Heterotermes indicola, *Reticulitermes flavipes, Reticulitermes* santonensis, *Reticulitermes* lucifugus, *Mastotermes* darwiniensis, *Zootermopsis* nevadensis, *Coptotermes formosanus.*
Bristle-tails such as Lepisma saccharina.

Industrial materials in the present context are understood as meaning non-living materials such as, preferably, polymers, adhesives, glues, paper and board, leather, wood, timber products and paints.

The material which is to be protected from insect attack is very particularly preferably wood and timber products.

Wood and timber products which can be protected by the composition according to the invention, or mixtures comprising it, are to be understood as meaning, for example:
construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound combination according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of turpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the insecticide/fungicide mixture is soluble or emulsifiable in this solvent mixture.

In a preferred embodiment, some of the organochemical solvent or solvent mixture is replaced by an aliphatic polar organochemical solvent or solvent mixture. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di-(2-ethylhexyl)-adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide and triflumuron, and also fimgicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The active compound combinations according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent stops in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the active compound combinations according to the invention, on their own or in combination with other active compounds, have an outstanding antifouling action.

Using the active compound combinations according to the invention on their own or in combination with other active compounds allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylene-bisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferable suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluor-folpet, 3-iodo-2-propinyl butyl-carbamate, tolylfluanid and azoles such as azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb;
or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalo-nitrile, tetramethylthiuram disulphide and 2,4,6-trichlorophenylmaleiimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments of colorants which are preferably insoluble in salt water. Paints may furthermore comprise materials such as colophonium to allow controlled release of the active compounds. Furthermore, the paints may comprise plasticizers, modifiers which affect the Theological properties and other conventional constituents. The compounds according to the invention or the abovementioned mixtures may also be incorporated into self-polishing antifouling systems.

The active compound combinations are also suitable for controlling animal pests, in particular insects, arachnids and mites, which are found in enclosed spaces such as, for example, dwellings, factory halls, offices, vehicle cabins and the like. They can be employed on their own or in combination with other active compounds and excipients in domestic insecticide products for controlling these pests. They are active against sensitive and resistant species and against all developmental stages.

These pests include:

From the order of the Scorpionidea, for example, Buthus occitanus.

From the order of the Acarina, for example, Argas persicus, Argas reflexus, *Bryobia* ssp., Dermanyssus gallinae, Glyciphagus domesticus, Ornithodorus moubat, Rhipicephalus sanguineus, Trombicula alfreddugesi, Neutrombicula autumnalis, *Dermatophagoides* pteronissimus, *Dermatophagoides* forinae.

From the order of the Araneae, for example, Avicularidae, Araneidae.

From the order of the Opiliones, for example, Pseudoscorpiones chelifer, Pseudoscorpiones cheiridium, Opiliones phalangium.

From the order of the Isopoda, for example, Oniscus asellus, Porcellio scaber.

From the order of the Diplopoda, for example, Blaniulus guttulatus, *Polydesmus* spp.

From the order of the Chilopoda, for example, *Geophilus* spp.

From the order of the Zygentoma, for example, *Ctenolepisma* spp., Lepisma saccharina, Lepismodes inquilinus.

From the order of the Blattaria, for example, *Blatta* orientalies, *Blattella germanica, Blattella* asahinai, Leucophaea maderae, *Panchlora* spp., *Parcoblatta* spp., *Periplaneta* australasiae, *Periplaneta americana, Periplaneta* brunnea, *Periplaneta* fuliginosa, Supella longipalpa.

From the order of the Saltatoria, for example, Acheta domesticus.

From the order of the Dermaptera, for example, Forficula auricularia.

From the order of the *Isoptera*, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., Latheticus oryzae, *Necrobia* spp., *Ptinus* spp., Rhizopertha dominica, *Sitophilus* granarius, *Sitophilus oryzae, Sitophilus zeamais*, Stegobium paniceum.

From the order of the *Diptera*, for example, *Aedes aegypti, Aedes albopictus, Aedes* taeniorhynchus, *Anopheles* spp., *Calliphora* erythrocephala, Chrysozona pluvialis, *Culex* quinquefasciatus, *Culex* pipiens, *Culex* tarsalis, *Drosophila* spp., Fannia canicularis, *Musca domestica, Phlebotomus* spp., *Sarcophaga* carnaria, *Simulium* spp., *Stomoxys* calcitrans, Tipula paludosa.

From the order of the *Lepidoptera*, for example, *Achroia* grisella, *Galleria mellonella, Plodia interpunctella*, Tinea cloacella, Tinea pellionella, *Tineola* bisselliella.

From the order of the *Siphonaptera*, for example, *Ctenocephalides* canis, *Ctenocephalides felis, Pulex* irritans, *Tunga* penetrans, *Xenopsylla* cheopis.

From the order of the *Hymenoptera*, for example, Camponotus herculeanus, Lasius fuliginosus, Lasius niger, Lasius umbratus, *Monomorium pharaonis, Paravespula* spp., Tetramorium caespitum.

From the order of the *Anoplura*, for example, Pediculus humanus capitis, Pediculus humanus corporis, Phthirus pubis.

From the order of the Heteroptera, for example, Cimex hemipterus, Cimex lectularius, Rhodnius prolixus, Triatoma infestans.

In the field of household insecticides, they are used alone or in combination with other suitable active compounds, suh as phosphonic acid esters, carbamates, pyrethroids, growth regulators or active compounds from other known classes of insecticides.

They are used as aerosols, pressureless spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

In fungicides and insecticides, a synergistic effect is always present when the fungicidal and insecticidal activity of the active compound combinations is greater than the sum of the activities of the active compounds applied on their own.

The expected activity for a given combination of two active compounds can be calculated as follows (cf. Colby, S.R., "Calculating Synergistic and Antagonistic Responses of Herbicide Combinations", Weeds 15, pages 20-22, 1967):

If

X is the efficacy, expresssed in % of the untreated control, when employing active compound A in a concentration of m ppm, Y is the efficacy, expressed in % of the untreated control, when employing active compound B in a concentration of n ppm, and E is the expected efficacy, expressed in % of the untreated control, when employing active compounds A and B in concentrations of m and n ppm, then $$E = X + Y - \frac{X \cdot Y}{100}.$$

If the actual fungicidal and insecticidal activity exceeds the calculated value, the activity of the combination is superadditive, i.e. a synergistic effect is present. In this case, the actually observed efficacy must exceed the value calculated for the expected efficacy (E) using the above formula.

EXAMPLE A

*Aphis gossypii* test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentrations.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed. The kill rates that have been determined are evaluated using Colby's formula.

In this test, for example, the following active compound combination in accordance with the present application shows a synergistically enhanced activity compared to the active compounds applied on their own:

TABLE A1 plant-damaging insects
*Aphis gossypii* test

| Active compounds | Concentration of active compound in ppm | Kill rate in % after $6^d$ |
|---|---|---|
| trifloxystrobin (I) | | |
| known imidacloprid (II) | 4 | 0 |
| known trifloxystrobin (I) + imidacloprid (II) (25:1) | 0.16 | 25 |
| | | found* calc.** |
| according to the invention | 4 + 0.16 | 95    25 |

*found = activity found
**calc. = activity calculated using Colby's formula

TABLE A2 plant-damaging insects
*Aphis gossypii* test

| Active compounds | Concentration of active compound in ppm | Kill rate in % after $6^d$ |
|---|---|---|
| trifloxystrobin (I) | | |
| known thiacloprid (III) | 20 | 0 |
| known trifloxystrobin (I) + thiacloprid (III) (25:1) | 0.8 | 55 |
| | | found* calc.** |
| according to the invention | 20 + 0.8 | 100    55 |

*found = activity found
**calc. = activity calculated using Colby's formula

TABLE A3 plant-damaging insects
*Aphis gossypii* test

| Active compounds | Concentration of active compound in ppm | Kill rate in % after $1^d$ |
|---|---|---|
| trifloxystrobin (I) | | |
| known acetamiprid (IV) | 4 | 0 |
| known trifloxystrobin (I) + acetamiprid (IV) (25:1) | 0.16 | 25 |
| | | calc.* found** |
| according to the invention | 4 + 0.16 | 85    25 |

*found = activity found
**calc. = activity calculated using Colby's formula

TABLE A4 plant-damaging insects
*Aphis gossypii* test

| Active compounds | Concentration of active compound in ppm | Kill rate in % after $1^d$ |
|---|---|---|
| trifloxystrobin (I) | | |
| known thiamethoxam (VI) | 20 | 0 |
| known trifloxystrobin (I) + thiamethoxam (VI) (25:1) | 0.8 | 25 |
| | | found* calc.** |
| according to the invention | 20 + 0.8 | 95    25 |

*found = activity found
**calc. = activity calculated using Colby's formula

TABLE A5 plant-damaging insects
*Aphis gossypii* test

| Active compounds | Concentration of active compound in ppm | Kill rate in % after $6^d$ |
|---|---|---|
| trifloxystrobin (I) | | |
| known dinotefuran (VIII) | 20 | 0 |
| known trifloxystrobin (I) + dinotefuran (VIII) (25:1) | 0.8 | 0 |
| | | found* calc.** |
| according to the invention | 20 + 0.8 | 70    0 |

*found = activity found
**calc. = activity calculated using Colby's formula

EXAMPLE B

*Myzus* test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of active compound of the desired concentration.

After the desired period of time, the kill in % is determined. 100% means that all aphids have been killed; 0% means that none of the aphids have been killed. The kill rates that have been determined are evaluated using Colby's formula.

In this test, for example, the following active compound combination in accordance with the present application shows a synergistically enhanced activity compared to the active compounds applied on their own:

TABLE B1 plant-damaging insects
*Myzus* test

| Active compounds | Concentration of active compound in ppm | Kill rate in % after $6^d$ | |
|---|---|---|---|
| trifloxystrobin (I) | | | |
| known imidacloprid (II) | 4 | 0 | |
| known trifloxystrobin (I) + imidacloprid (II) (25:1) | 0.16 | 25 | |
| | | found* | calc.** |
| according to the invention | 4 + 0.16 | 99 | 25 |

*found = activity found
**calc. = activity calculated using Colby's formula

TABLE B2 plant-damaging insects
*Myzus* test

| Active compounds | Concentration of active compound in ppm | Kill rate in % after $6^d$ | |
|---|---|---|---|
| trifloxystrobin (I) | | | |
| known thiacloprid (III) | 20 | 0 | |
| known trifloxystrobin (I) + thiacloprid (III) (25:1) | 0.8 | 85 | |
| | | found* | calc.** |
| according to the invention | 20 + 0.8 | 100 | 85 |

*found = activity found
**calc. = activity calculated using Colby's formula

TABLE B3 plant-damaging insects
*Myzus* test

| Active compounds | Concentration of active compound in ppm | Kill rate in % after $6^d$ | |
|---|---|---|---|
| trifloxystrobin (I) | | | |
| known acetamiprid (IV)-- | 4 | 0 | |
| known trifloxystrobin (I) + acetamiprid (IV) (25:1) | 0.16 | 20 | |
| | | found* | calc.** |
| according to the invention | 4 + 0.16 | 98 | 20 |

*found = activity found
**calc. = activity calculated using Colby's formula

TABLE B4 plant-damaging insects
*Myzus* test

| Active compounds | Concentration of active compound in ppm | Kill rate in % after $6^d$ | |
|---|---|---|---|
| trifloxystrobin (I) | | | |
| known thiamethoxam (VI) | 4 | 0 | |
| known trifloxystrobin (I) + thiamethoxam (VI) (25:1) | 0.16 | 15 | |
| | | found* | calc.** |
| according to the invention | 4 + 0.16 | 95 | 15 |

*found = activity found
**calc. = activity calculated using Colby's formula

TABLE B5 plant-damaging insects
*Myzus* test

| Active compounds | Concentration of active compound in ppm | Kill rate in % after $6^d$ | |
|---|---|---|---|
| trifloxystrobin (I) | | | |
| known chlothianidin (VII) | 20 | 0 | |
| known trifloxystrobin (I) + chlothianidin (VII) (25:1) | 0.8 | 95 | |
| | | found* | calc.** |
| according to the invention | 20 + 0.8 | 100 | 95 |

*found = activity found
**calc. = activity calculated using Colby's formula

TABLE B6 plant-damaging insects
*Myzus* test

| Active compounds | Concentration of active compound in ppm | Kill rate in % after $6^d$ | |
|---|---|---|---|
| trifloxystrobin (I) | | | |
| known dinotefuran (VIII) | 100 | 10 | |
| known trifloxystrobin (I) + dinotefuran (VIII) (25:1) | 4 | 0 | |
| | | found* | calc.** |
| according to the invention | 100 + 4 | 95 | 10 |

*found = activity found
**calc. = activity calculated using Colby's formula

EXAMPLE C

*Phaedon* larvae test

| | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (Phaedon cochleariae) while the leaves are still moist.

After the desired period of time, the kill in % is determined. 100% means that all beetle larvae have been killed; 0% means that none of the beetle larvae have been killed. The kill rates that have been determined are evaluated using Colby's formula.

In this test, for example, the following active compound combination in accordance with the present application shows a synergistically enhanced activity compared to the active compounds applied on their own:

TABLE C1 plant-damaging insects
*Phaedon larvae* test

| Active compounds | Concentration of active compound in ppm | Kill rate in % after $3^d$ | |
|---|---|---|---|
| trifloxystrobin (I) | | | |
| known imidacloprid (II) | 100 | 0 | |
| known trifloxystrobin (I) + imidacloprid (II) (25:1) | 4 | 35 | |
| | | found* | calc.** |
| according to the invention | 100 + 4 | 100 | 35 |

*found = activity found
**calc. = activity calculated using Colby's formula

TABLE C2 plant-damaging insects
*Phaedon larvae* test

| Active compounds | Concentration of active compound in ppm | Kill rate in % after $3^d$ | |
|---|---|---|---|
| trifloxystrobin (I) | | | |
| known thiacloprid (III) | 100 | 0 | |
| known trifloxystrobin (I) + thiacloprid (III) (25:1) | 4 | 10 | |
| | | found* | calc.** |
| according to the invention | 100 + 4 | 100 | 10 |

*found = activity found
**calc. = activity calculated using Colby's formula

TABLE C3 plant-damaging insects
*Phaedon larvae* test

| Active compounds | Concentration of active compound in ppm | Kill rate in % after $3^d$ | |
|---|---|---|---|
| trifloxystrobin (I) | | | |
| known acetamiprid (IV) | 100 | 5 | |
| known | 4 | 5 | |

TABLE C3-continued plant-damaging insects
*Phaedon larvae* test

| Active compounds | Concentration of active compound in ppm | Kill rate in % after $3^d$ | |
|---|---|---|---|
| trifloxystrobin (I) + acetamiprid (IV) (25:1) | | | |
| | | found* | calc.** |
| according to the invention | 100 + 4 | 85 | 9.75 |

*found = activity found
**calc. = activity calculated using Colby's formula

TABLE C4 plant-damaging insects
*Phaedon larvae* test

| Active compounds | Concentration of active compound in ppm | Kill rate in % after $3^d$ | |
|---|---|---|---|
| trifloxystrobin (I) | | | |
| known thiamethoxam (VI) | 100 | 5 | |
| known trifloxystrobin (I) + thiamethoxam (VI) (25:1) | 4 | 40 | |
| | | found* | calc.** |
| according to the invention | 100 + 4 | 100 | 43 |

*found = activity found
**calc. = activity calculated using Colby's formula

TABLE C5 plant-damaging insects
*Phaedon larvae* test

| Active compounds | Concentration of active compound in ppm | Kill rate in % after $3^d$ | |
|---|---|---|---|
| trifloxystrobin (I) | | | |
| known chlothianidin (VII) | 100 | 5 | |
| known trifloxystrobin (I) + chlothianidin (VII) (25:1) | 4 | 30 | |
| | | found* | calc.** |
| according to the invention | 100 + 4 | 90 | 33.5 |

*found = activity found
**calc. = activity calculated using Colby's formula

TABLE C6 plant-damaging insects
*Phaedon larvae* test

| Active compounds | Concentration of active compound in ppm | Kill rate in % after $3^d$ | |
|---|---|---|---|
| trifloxystrobin (I) | | | |
| known dinotefuran (VIII) | 100 | 0 | |
| known trifloxystrobin (I) + dinotefuran (VIII) (25:1) | 4 | 5 | |
| | | found* | calc.** |
| according to the invention | 100 + 4 | 100 | 5 |

*found = activity found
**calc. = activity calculated using Colby's formula

EXAMPLE D

| Spodoptera frugiperda test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed. The kill rates that have been determined are evaluated using Colby's formula.

In this test, for example, the following active compound combination in accordance with the present application shows a synergistically enhanced activity compared to the active compounds applied on their own:

TABLE D1 plant-damaging insects
*Spodoptera frugiperda* test

| Active compounds | Concentration of active compound in ppm | Kill rate in % after $3^d$ | |
|---|---|---|---|
| trifloxystrobin (I) | | | |
| known imidacloprid (II) | 100 | 0 | |
| known | 4 | 0 | |
| trifloxystrobin (I) + imidacloprid (II) (25:1) | | | |
| | | found* | calc.** |
| according to the invention | 100 + 4 | 85 | 0 |

*found = activity found
**calc. = activity calculated using Colby's formula

TABLE D2 plant-damaging insects
*Spodoptera frugiperda* test

| Active compounds | Concentration of active compound in ppm | Kill rate in % after $3^d$ | |
|---|---|---|---|
| trifloxystrobin (I) | | | |
| known thiacloprid (III) | 100 | 0 | |
| known | 4 | 0 | |
| trifloxystrobin (I) + thiacloprid (III) (25:1) | | | |
| | | found* | calc.** |
| according to the invention | 100 + 4 | 80 | 0 |

*found = activity found
**calc. = activity calculated using Colby's formula

TABLE D3 plant-damaging insects
*Spodoptera frugiperda* test

| Active compounds | Concentration of active compound in ppm | Kill rate in % after $3^d$ | |
|---|---|---|---|
| trifloxystrobin (I) | | | |
| known acetamiprid (IV) | 100 | 5 | |
| known | 4 | 65 | |
| trifloxystrobin (I) + acetamiprid (IV) (25:1) | | | |
| | | found* | calc.** |
| according to the invention | 100 + 4 | 100 | 66.75 |

*found = activity found
**calc. = activity calculated using Colby's formula

TABLE D4 plant-damaging insects
*Spodoptera frugiperda* test

| Active compounds | Concentration of active compound in ppm | Kill rate in % after $3^d$ | |
|---|---|---|---|
| trifloxystrobin (I) | | | |
| known thiamethoxam (VI) | 100 | 5 | |
| known | 4 | 15 | |
| trifloxystrobin (I) + thiamethoxam (VI) (25:1) | | | |
| | | found* | calc.** |
| according to the invention | 100 + 4 | 65 | 19.25 |

*found = activity found
**calc. = activity calculated using Colby's formula

TABLE D5 plant-damaging insects
*Spodoptera frugiperda* test

| Active compounds | Concentration of active compound in ppm | Kill rate in % after $3^d$ | |
|---|---|---|---|
| trifloxystrobin (I) | | | |
| known chlothianidin (VII) | 100 | 0 | |
| known | 4 | 85 | |
| trifloxystrobin (I) + chlothianidin (VII) (25:1) | | | |
| | | found* | calc.** |
| according to the invention | 100 + 4 | 100 | 85 |

*found = activity found
**calc. = activity calculated using Colby's formula

TABLE D6 plant-damaging insects
*Spodoptera frugiperda* test

| Active compounds | Concentration of active compound in ppm | Kill rate in % after $6^d$ |
|---|---|---|
| trifloxystrobin (I) | | |
| known | 100 | 0 |

TABLE D6-continued plant-damaging insects
*Spodoptera frugiperda* test

| Active compounds | Concentration of active compound in ppm | Kill rate in % after $6^d$ | |
|---|---|---|---|
| dinotefuran (VIII) | | | |
| known | 4 | 70 | |
| trifloxystrobin (I) + dinotefuran (VIII) (25:1) | | | |
| | | found* | calc.** |
| according to the invention | 100 + 4 | 100 | 70 |

*found = activity found
**calc. = activity calculated using Colby's formula

EXAMPLE E

| *Plutella* test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamond back moth (*Plutella xylostella*, sensitive strain) while the leaves are still moist.

After the desired period of time, the kill in % is determined. 100% means that all caterpillars have been killed; 0% means that none of the caterpillars have been killed. The kill rates that have been determined are evaluated using Colby's formula.

In this test, for example, the following active compound combination in accordance with the present application shows a synergistically enhanced activity compared to the active compounds applied on their own:

TABLE E1 plant-damaging insects
*Plutella* test

| Active compounds | Concentration of active compound in ppm | Kill rate in % after $3^d$ | |
|---|---|---|---|
| trifloxystrobin (I) | | | |
| known | 100 | 0 | |
| acetamiprid (IV) | | | |
| known | 4 | 0 | |

TABLE E1-continued plant-damaging insects
*Plutella* test

| Active compounds | Concentration of active compound in ppm | Kill rate in % after $3^d$ | |
|---|---|---|---|
| trifloxystrobin (I) + acetamiprid (IV) (25:1) | | | |
| | | found* | calc.** |
| according to the invention | 100 + 4 | 60 | 0 |

*found = activity found
**calc. = activity calculated using Colby's formula

What is claimed is:

1. An active compound combination comprising synergistically effective amounts of a compound of the formula (I)

(I)

[Chemical structure of trifloxystrobin]

and a compound of formula (II)

(II)

[Chemical structure of imidacloprid-type compound with pyridine, CN, imidazolidine ring, and N—NO₂]

wherein the weight ratio of the active compound of formula (I) to the active compound of the formula (II) is from 1:0.04 to 1:10.

2. An active compound combination according to claim 1 wherein the weight ratio of the active compound of formula (I) to the active compound of the formula (II) is from 1:0.1 to 1:10.

3. The active compound combination according to claim 1, wherein the weight ratio of the active compound of formula (I) to the active compound of the formula (II) is from 1:0.2 to 1:2.

4. A fungicidal or insecticidal composition comprising an effective amount of an active compound combination according to claim 1 and one or more extenders and/or surfactants.

5. A process for preparing a fungicidal or insecticidal composition comprising mixing an active compound combination according to claim 1 with one or more extenders and/or surfactants.

\* \* \* \* \*